United States Patent [19]
Stanek et al.

[11] Patent Number: 4,839,379
[45] Date of Patent: * Jun. 13, 1989

[54] SUBSTITUTED AZABICYCLOALKANES, THE USE THEREOF, PHARMACEUTICAL COMPOSITIONS CONTAINING THEM

[75] Inventors: Jaroslav Stanek, Birsfelden; Ernst Schweizer, Arlesheim, both of Switzerland

[73] Assignee: Ciba-Geigy Corporation, Ardsley, N.Y.

[*] Notice: The portion of the term of this patent subsequent to Jun. 30, 2004 has been disclaimed.

[21] Appl. No.: 80,240

[22] Filed: Jul. 28, 1987

Related U.S. Application Data

[63] Continuation of Ser. No. 758,835, Jul. 24, 1985, abandoned, which is a continuation of Ser. No. 562,258, Dec. 16, 1983, abandoned.

[30] Foreign Application Priority Data

Dec. 21, 1982 [CH] Switzerland .................. 7450/82

[51] Int. Cl.⁴ .................. C07D 221/22; A61K 31/435
[52] U.S. Cl. .................. 514/421; 514/412; 514/299; 548/452; 548/453
[58] Field of Search .............. 514/299, 412, 418, 421; 548/452, 453

[56] References Cited

U.S. PATENT DOCUMENTS

| | | | |
|---|---|---|---|
| 2,673,205 | 3/1954 | Hoffmann et al. | 260/281 |
| 2,848,455 | 8/1958 | Hoffmann et al. | 260/281 |
| 3,166,571 | 1/1965 | Izzo et al. | 260/326.5 |
| 3,621,012 | 11/1971 | Starchen et al. | 548/453 |
| 4,131,611 | 12/1978 | Fanshaw et al. | 260/326.8 |
| 4,164,404 | 8/1979 | Los et al. | 548/453 |
| 4,231,935 | 11/1980 | Fanshaw et al. | 260/326.5 B |
| 4,289,762 | 9/1981 | Metcalf et al. | 424/242 |
| 4,322,416 | 3/1982 | Metcalf et al. | 424/242 |
| 4,435,419 | 3/1984 | Epstein et al. | 548/452 |
| 4,677,129 | 6/1987 | Alds et al. | 514/299 |

FOREIGN PATENT DOCUMENTS

| | | |
|---|---|---|
| 548074 | 11/1956 | Belgium . |
| 3121153 | 12/1982 | Fed. Rep. of Germany . |
| 1015618 | 1/1966 | United Kingdom . |

OTHER PUBLICATIONS

De Vita et al., Cancer, pp. 914–916 (1982).
Pharmanual 2, Aminoglutethimide, pp. 126–127 (1981).
CA 94:168315w, Abul-Hajj, Abstract of J. Steroid Biochem. 13(12), 1395–400.
CA 91:168933j, Brodie et al., Abstract of J. Steroid Biochem. 11(1A), 107–12 (1979).
CA 92:195083j, Brodie, Abstract of J. Endocrinol Invest. 2(4), 445–60 (1979).
CA 93:61986t, Budnick et al., Steroids 35(5), 533–41.
Epstein et al., J. Med. Chem., 24, 481 (1981).
Chemical Abstracts, vol. 99, 22310x (1983).
Chemical Abstracts, vol. 89, 6216j (1978).
Chemical Abstracts, vol. 101, 38344g (1984).
Alder et al., Helv. Cim. Acta, vol. 65, pp. 2405–2412 (1982).
Alder et al., J. Am. Chem. Soc., vol. 105, pp. 6712–6714 (1983).
J. March, Advanced Organic Chemistry, pp. 130, 131, 133.
Morrison et al., Organic Chemistry 5th ed., pp. 441–445.
Roberts et al., 2nd ed., Basic Principles of Chem., pp. 462–467.
Journal of Chemical Education, vol. 40, No. 10, pp. 504–511, No. 11, pp. 599–603 (1963).

Primary Examiner—Nichola S. Rizzo
Attorney, Agent, or Firm—Irving M. Fishman; JoAnn Villamizar

[57] ABSTRACT

1-Phenyl-3-azabicyclo[3.1.0]hexane-2,4-diones of the formula

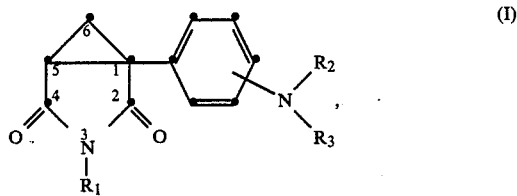

wherein $R_1$ is hydrogen, $R_2$ is hydrogen, sulfo or acyl and $R_3$ is hydrogen, or $R_1$ is a saturated or unsaturated aliphatic, cycloaliphatic or cycloaliphatic-aliphatic carbon radical of up to and including 18, preferably of up to and including 12, carbon atoms, $R_2$ is hydrogen, lower alkyl, sulfo or acyl and $R_3$ is hydrogen or lower alkyl, and to salts thereof, and salts thereof, have valuable pharmacological properties and are effective aromatase inhibitors. They can therefore be used for the treatment of hormonal diseases, in particular mammary carcinomas.

16 Claims, No Drawings

SUBSTITUTED AZABICYCLOALKANES, THE USE THEREOF, PHARMACEUTICAL COMPOSITIONS CONTAINING THEM

This application is a continuation of application Ser. No. 758,835, filed 7/24/85 now abandoned, which is a continuation of Ser. No. 562,258 filed 12/16/83 now abandoned.

The present invention relates to novel aminophenyl-substituted azabicycloalkanes having valuable pharmacological properties and to salts thereof, to the use of these novel compounds and of pharmaceutical compositions which contain them, to the pharmaceutical compositions themselves and to processes for the preparation of the novel compounds, as well as to intermediates and to the preparation thereof.

1-Phenyl-3-azabicyclo[3.1.0]hexane-2,4-dione compounds which are substituted at the phenyl ring by halogen, $C_1$–$C_6$alkylamino or di($C_1$–$C_6$)alkylamino are disclosed as intermediates in German Offenlegungsschrift No. 32 23 463 without any disclosure of pharmaceutical properties. These compounds are converted by reduction into the corresponding antidepressive 1-phenyl-3-azabicyclo[3.1.0]hexane compounds.

The present invention relates to substituted 1-phenyl-3-azabicyclo[3.1.0]hexane-2,4-diones of the formula

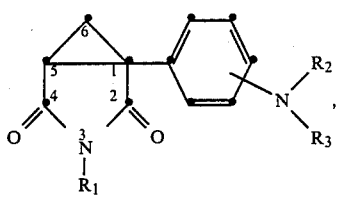

(I)

wherein $R_1$ is hydrogen, $R_2$ is hydrogen, sulfo or acyl and $R_3$ is hydrogen, or $R_1$ is a saturated or unsaturated aliphatic, cycloaliphatic or cycloaliphatic-aliphatic carbon radical of up to and including 18, preferably of up to and including 12, carbon atoms, $R_2$ is hydrogen, lower alkyl, sulfo or acyl and $R_3$ is hydrogen or lower alkyl, and to salts thereof.

The invention also relates to pharmaceutical compositions which contain compounds of formula I, wherein $R_1$ is hydrogen, $R_2$ is hydrogen or lower alkyl, and $R_3$ is lower alkyl, and to the use of these compounds in a method of treating humans and animals.

Throughout this specification, the term "lower" used to qualify groups or radicals, e.g. lower alkyl, lower alkoxy, lower alkanoyl and the like, will be understood as meaning that, unless otherwise explicitly indicated, the groups and radicals so defined contain up to and including 7, preferably up to and including 4, carbon atoms.

The terms and expressions generally employed throughout this specification will be understood as having preferably the following meanings.

A saturated or unsaturated aliphatic, cycloaliphatic or cycloaliphatic-aliphatic hydrocarbon radical $R_1$ is e.g. alkyl, alkenyl, lower alkynyl, cycloalkyl, cycloalkenyl, cycloakyl-lower alkyl, cycloalkyl-lower alkenyl or cycloalkenyl-lower alkyl.

Alkyl $R_1$ contains e.g. 1 to 2 carbon atoms and is, for example, lower alkyl of 1 to 7 carbon atoms such as methyl, ethyl, n-propyl, isopropyl, n-butyl, isobutyl, tert-butyl, n-pentyl, neopentyl, n-hexyl or n-heptyl, as well as n-octyl, n-nonyl, n-decyl, n-undecyl or n-dodecyl.

Alkenyl $R_1$ contains e.g. 1 to 12 carbon atoms and is for example lower alkenyl of 1 to 7 carbon atoms, e.g. vinyl, allyl or 2- or 3-butenyl, as well as 1-octenyl, 1-nonenyl, 1-decenyl, 1-undecenyl or 1-dodecenyl, in which the double bond can also be in a position other than the 1-position.

Lower alkynyl $R_1$ contains e.g. 2 to 7, preferably 2 to 4, carbon atoms, and is e.g. ethynyl, 1-propynyl or 2-propynyl.

Cycloalkyl $R_1$ contains e.g. 3 to 10, preferably 3 to 6, carbon atoms, and is e.g. cyclopropyl, cyclobutyl, cyclopentyl or cyclohexyl.

Cycloalkenyl $R_1$ contains e.g. 3 to 10, preferably 3 to 6, carbon atoms, and is e.g. 1-cyclohexenyl or 1,4-cyclohexadienyl.

Cycloalkyl-lower alkyl $R_1$ contains e.g. 4 to 10, preferably 4 to 7, carbon atoms, and is e.g. cyclopropylmethyl, cyclobutylmethyl, cyclopentylmethyl or cyclohexylmethyl, as well as 2-cyclopropylethyl, 2-cyclobutylethyl, 2-cyclopentylethyl or 2-cyclohexylethyl.

Cycloalkyl-lower alkenyl $R_1$ contains e.g. 5 to 10, preferably 4 to 9, carbon atoms, and is e.g. cyclohexylvinyl or cyclohexylallyl.

Cycloalkenyl-lower alkyl $R_1$ contains e.g. 4 to 10, preferably 4 to 8, carbon atoms, and is e.g. 1-cyclohexenylmethyl or 1,4-cyclohexadienylmethyl, as well as 2-(1-cyclohexenyl)ethyl or 2-(1,4-cyclohexadienyl)ethyl.

Lower alkyl $R_2$ or $R_3$ is as defined for $R_1$ and is preferably methyl or ethyl.

Acyl $R_2$ contains e.g. up to 19 carbon atoms inclusive and is derived from a carboxylic acid, a hemiester of carbonic acid, from carbamic acid, a substituted carbamic acid, a sulfonic acid, amidosulfonic acid or from a substituted amidosulfonic acid.

Acyl $R_2$ has e.g. the formulae: $R^b$—CO—, $R^a$—O—CO—, $(R^b)(R^b)$N—CO—, $R^b$—SO$_2$— or $(R^b)(R^b)$N—SO$_2$—, wherein $R^a$ is a saturated or unsaturated aliphatic, cycloaliphatic or cycloaliphatic-aliphatic hydrocarbon radical of up to and including 18 carbon atoms, preferably of up to and including 10 carbon atoms, or is an aromatic or aromatic-aliphatic hydrocarbon radical of up to and including 18, preferably of up to and including 10, carbon atoms, and $R^b$ is hydrogen or has the meanings of $R^a$.

A saturated or unsaturated aliphatic, cycloaliphatic or cycloaliphatic-aliphatic hydrocarbon radical $R^a$ or $R^b$ is as defined for $R_1$ and is preferably lower alkyl, e.g. methyl or ethyl.

An aromatic or aromatic-aliphatic hydrocarbon radical $R^a$ or $R^b$ is e.g. phenyl, phenyl-lower alkyl, e.g. benzyl, or diphenylmethyl.

Acyl $R_2$ is preferably lower alkanoyl, e.g. formyl or acetyl, or is lower alkanesulfonyl, e.g. methanesulfonyl or ethanesulfonyl.

Salts of compounds of the formula I which contain a salt-forming group are, in particular, pharmaceutically acceptable non-toxic salts.

Such salts are formed e.g. from the amino group at the phenyl ring by addition of an inorganic acid, e.g. hydrochloric acid, sulfuric acid or phosphoric acid, and are e.g. hydrochlorides, hydrogen sulfates, hydrogen phosphates or dihydrogen phosphates.

Further acid addition salts are formed e.g. from carboxylic acids and are, for example, formates, acetates, trifluoroacetates, benzoates or salicylates.

The compounds of formula I may also be obtained in the form of hydrates.

In an alphabetically increasing order of preference, the invention relates to the following compounds of formula I:

(a) compounds of the formula I, wherein $R_1$ is hydrogen, $R_2$ is hydrogen, sulfo, lower alkanoyl or lower alkanesulfonyl, and $R_3$ is hydrogen, or $R_1$ is alkyl, alkenyl, lower alkynyl, cycloalkyl, cycloalkenyl, cycloalkyl-lower alkyl, cycloalkyl-lower alkenyl or cycloalkenyl-lower alkenyl, $R_2$ is hydrogen, lower alkyl, sulfo, lower alkanoyl or lower alkanesulfonyl, and $R_3$ is hydrogen or lower alkyl, and salts thereof, in particular pharmaceutically acceptable salts;

(b) compounds of the formula I, wherein $R_1$, $R_2$ and $R_3$ are hydrogen or wherein $R_1$ is alkyl, e.g. lower alkyl such as methyl, ethyl, n-propyl, isopropyl, n-butyl, isobutyl, tert-butyl, n-pentyl, neopentyl, n-hexyl or n-heptyl, as well as n-octyl, n-nonyl or n-decyl, lower alkenyl such as vinyl or allyl, lower alkynyl such as ethynyl, 1-propynyl or 2-propynyl, cycloalkyl such as cyclopropyl, cyclopentyl or cyclohexyl, or cycloalkyl-lower alkyl such as cyclopentylmethyl or cyclohexylmethyl, $R_2$ is hydrogen or lower alkyl, e.g. methyl, and $R_3$ is hydrogen or lower alkyl, e.g. methyl, and salts thereof, especially pharmaceutically acceptable salts thereof;

(c) compounds of the formula I, wherein $R_1$ is hydrogen, lower alkyl, e.g. methyl, ethyl, n-propyl, isopropyl, n-butyl, isobutyl, tertbutyl, n-pentyl, neopentyl, n-hexyl or n-heptyl, lower alkenyl, e.g. vinyl or allyl, lower alkynyl, e.g. ethynyl or 1- or 2-propynyl, cycloalkyl, e.g. cyclohexyl, cycloalkyl-lower alkyl, e.g. cyclohexymethyl, and $R_2$ and $R_3$ are hydrogen, and pharmaceutically acceptable salts thereof;

(d) compounds of the formula I, wherein $R_1$ is hydrogen, lower alkyl, e.g. methyl, ethyl, n-propyl, isopropyl, n-butyl, isobutyl or tert-butyl, lower alkenyl, e.g. vinyl or allyl, lower alkynyl, e.g. ethynyl or 1- or 2-propynyl, cycloalkyl-lower alkyl, e.g. cyclohexylmethyl; the group $—N(R_2)(R_3)$ is in the 4-position of the phenyl radical and $R_2$ and $R_3$ are hydrogen, and pharmaceutically acceptable salts thereof.

Most particularly, the present invention relates to the compounds referred to in the Examples.

The novel compounds of formula I and their pharmaceutically acceptable salts have, for example, valuable pharmacological properties as aromatase inhibitors. The suitability of compounds of formula I as aromatase inhibitors can be demonstrated in the aromatase assay according to P. E. Graves and H. A. Salhanick, Endrocrinology, Vol. 105, page 52 (1979), by using human placental microsomes in vitro. In this experimental method, the formation of water with tritium isotopes and 17β-oestradiol obtained from [1β,2β—³H]-testosterone is measured as a result of the action of a compound of the formula I on the formation of the hydrogenated form of the aromatase coenzyme, nicotinamide adenine dinucleotide phosphate (NADPH). The addition of a compound of the formula I, e.g. of 1-(4-aminophenyl)-3-cyclohexylmethyl-3-azabicyclo[3.1.0]hexane-2,4-dione, substantially reduces the enzyme activity (NADPH content), resulting in a markedly lower content of water with radioactive tritium isotopes than with measurements made without the addition of a compound of the formula I. Comparison measurements show, moreover, that the diminution of enzyme activity resulting from the addition of a compound of the formula I, e.g. of 1-(4-aminophenyl)-3-cyclohexylmethyl-3-azabicyclo[3.1.0]hexane-2,4-dione, is substantially greater than with the addition of other known aromatase inhibitors, e.g. aminoglutethimide.

On account of their activity as aromatase inhibitors, the compounds of the formula I, wherein $R_1$ is hydrogen or a saturated or unsaturated aliphatic, cycloaliphatic or cycloaliphatic-aliphatic hydrocarbon radical of up to and including 18, preferably up to and including 12, carbon atoms, $R_2$ is hydrogen, lower alkyl, sulfo or acyl, and $R_3$ is hydrogen or lower alkyl, or salts thereof, can be used as medicaments, for example in the form of pharmaceutical compositions, for the treatment of hormonal diseases, e.g. hormonal tumours, especially mammary carcinoma, and anomalies, e.g. gynecomastia, in warm-blooded animals (humans and animals), by enteral, e.g. oral, or parenteral administration of therapeutically effective doses.

The use of the these compounds as medicaments, especially with carcinostatic activity, in one of the methods referred to above for treatment of the human or animal body, also falls within the scope of the invention.

The daily doses of such compounds are from about 1 mg to 100 mg, preferably from 5 mg to about 50 mg/kg of body weight, for mammals, depending on the species, and also for persons, depending on age, individual condition and mode of application. For parenteral administration, e.g. intramuscular or subcutaneous injection, or intravenous infusion, the doses within this range are in general lower than in enteral, i.e. oral or rectal, administration. The compounds of formula I, and pharmaceutically acceptable salts of such compounds with salt-forming properties, are administered orally or rectally, preferably in dosage unit formulations such as tablets, dragées, capsules or suppositories, and parenterally in particular in the form of injectable solutions, emulsions or suspensions, or of infusion solutions, with suitable solutions being in particular salt solutions.

The invention further relates to pharmaceutical compositions for enteral, e.g. oral or rectal, administration, or for parenteral administration, which compositions comprise a therapeutically effective amount of a compound of the formula I, or of a pharmaceutically acceptable salt of such a compound having a salt-forming group, optionally together with a pharmaceutically acceptable carrier or mixture of carriers. Solid or liquid inorganic or organic substances are used as carriers. Appropriate dosage unit formulations, especially for peroral administration, e.g. dragées, tablets or capsules, preferably contain about 50 mg to 500 mg, most preferably about 100 to 400 mg, of a compound of the formula I or of a pharmaceutically acceptable salt of such a compound which is capable of salt formation, together with pharmaceutically acceptable carriers.

Suitable carriers are in particular fillers such as sugar, for example lactose, saccharose, mannitol or sorbitol, cellulose preparations and/or calcium phosphates, e.g. tricalciumphosphate or calcium bisphosphate, and also binders such as starch pastes, e.g. maize, corn, rice or potato starch, gelatin, tragacanth, methyl cellulose and/or, if desired, disintegrators, such as the abovementioned starches, also carboxymethyl starch, crosslinked polyvinylpyrrolidone, agar, alginic acid or a salt thereof such as sodium alginate. Adjuncts are in particular glidants and lubricants, for example silica, talc, stearic acid or salts thereof such as magnesium stearate or calcium stearate, and/or polyethylene glycol, Dragée cores are provided with suitable coatings which can be resistant to gastric juices, using inter alia concentrated sugar solutions which may contain gum arabic, talc, polyvinylpyrrolidone, polythylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropylmethylcellulose phthalate. Dyes or pigments can be added to the tablets or dragée coatings, for example to identify or indicate different doses of active ingredient.

Further pharmaceutical compositions for oral administration are dry-filled capsules made of gelatin and also soft sealed capsules consisting of gelatin and a plasticiser such as glycerol or sorbitol. The dry-filled capsules can contain the active ingredient in the form of granules, for example in admixture with fillers such as lactose, binders such as starches and/or glidants such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols. It is also possible to use gelatin rectal capsules which contain a combination of the active ingredient with a base material. Suitable base materials are e.g. liquid triglycerides, polyethylene glycols and paraffin hydrocarbons.

Particularly suitable dosage forms for parenteral administration are aqueous solutions of an active ingredient in water-soluble form, for example a water-soluble salt, and also suspensions of the active ingredient, such as corresponding oily injections suspensions, for which there are used suitable lipophilic solvents or vehicles such as fatty oils, for example sesame oil, or synthetic fatty acid esters, for example ethyl oleate or triglycerides, or aqueous injections suspensions which contain substances which increase the viscosity, for example sodium carboxymethylcellulose, sorbitol and/or dextran, and optionally also stabilisers.

The pharmaceutical compositions of the present invention are prepared in a manner known per se, for example by conventional mixing, granulating, confectioning, dissolving or lyophilising methods. For example, pharmaceutical compositions for oral administration can be obtained by combining the active ingredient with solid carriers, optionally granulating a resulting mixture and processing the mixture or granulate, if desired or necessary after the addition of suitable adjuncts, to tablets or dragée cores.

The present invention also relates to processes for the preparation of compounds of the formula I. These compounds can be prepared by methods which are known per se, e.g.

(a) by converting X into the

group in a compound of the formula

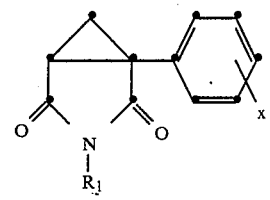

(II)

wherein $R_1$ is as defined for formula I and X is a group which can be converted into the

group, or in a salt thereof, or (b) cyclising a compound of the formula

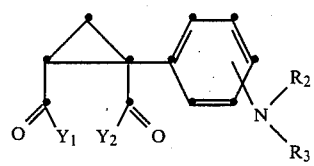

(III)

wherein $R_2$ and $R_3$ are as defined for formula I, $Y_1$ and $Y_2$ are leaving groups, or a salt thereof, by reaction with a compound which introduces the group

or (c) by addition of —CH$_2$—(methylene) to the double bond of the maleimide in a compound of the formula

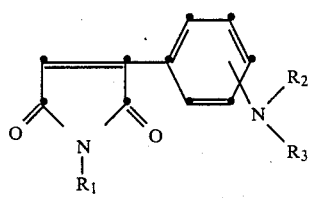

(IV)

wherein $R_1$, $R_2$ and $R_3$ are as defined for formula I, or in a salt thereof, and, if desired, converting a compound of the formula I into another compound of the formula I and/or converting a salt into the free compound or into another salt, and/or converting a free compound into a salt and/or separating a mixture of isomers into the individual isomers.

Process (a)

In a compound of the formula II, a group X which can be converted into the

group is e.g. a nitrogen-containing reducible group, e.g. the nitro, nitroso, hydroxylamino or azido group, a replaceable group, e.g. halogen such as chlorine, bromine or iodine, or a derived carboxyl group, or a protected amino group from which the protective group is removed and replaced by hydrogen.

A nitrogen-containing reducible group, e.g. the nitro, nitroso, hydroxylamino or azido group, is converted into the amino group by a conventional reducing agent which, if desired, is used in the presence of a suitable catalyst and/or carrier.

A suitable reducing agent is in particular: catalytically activated hydrogen, the hydrogenation catalyst being e.g. a noble metal catalyst such as a palladium, platinum, rhodium or nickel catalyst, or a noble metal compound, e.g. platinum dioxide, and which is used, if desired, with a suitable carrier such as carbon, barium sulfate or barium carbonate or calcium carbonate, a reducing tin(II) or iron(II) salt, e.g. as chloride and, in the latter case, also as sulfate, a reducing dithionite or sulfite salt, e.g. sodium dithionite, sodium sulfite or sodium bisulfite, an inert or activated metal, e.g. activated iron, tin, zinc or aluminium, which may be activated in the presence of the corresponding metal salt or of a neutral salt, e.g. calcium, magnesium, potassium or sodium chloride, and also a sulfide, e.g. hydrogen sulfide, a di- or polysulfide, e.g. sodium disulfide or sodium polysulfide, an alkali metal sulfide or alkaline earth metal bisulfide, e.g. sodium sulfide or sodium bisulfide, ammonium sulfide or ammonium polysufide, a reducing hydrogen donor, e.g. unsubstituted or substituted hydrazine, for example hydrazine or phenylhydrazine, which may be added in the form of an acid addition salt, e.g. as hydrochloride, or molecular hydrogen from which the charge is removed by reduction at the cathode.

The reduction with catalytically activated hydrogen is carried out under normal or elevated pressure, e.g. at about 5 atoms. The reduction with the above mentioned reducing agents is carried out in acid medium, e.g. in acetic acid medium, or in neutral medium. The reduction with iron(II) salts is carried out under basic conditions, in which reaction the reducing iron(II) hydroxide precipitates. The reductions with dithionite salts and sulfides also take place under basic conditions.

The reduction with hydrogen donors, e.g. hydrazines, is speeded up by means of the hydrogen catalysts referred to above, e.g. Raney nickel, palladium on carbon or platinum. The electrolytic reduction of the nitro groups to the amine is carried out at cathodes made of metals with high overpotential, e.g. lead, tin, nickel, copper or zinc. The electrolysis is normally carried out in sulfuric acid or hydrochloric acid medium.

The above mentioned reducing agents are added in at least equimolar amount and preferably in excess. The addition of an excess of reducing agent will prevent the formation of intermediates, e.g. nitroso or hydroxylamino compounds.

The reduction is preferably carried out in a solvent, e.g. a lower alkanol, e.g. methanol or ethanol, a lower alkanecarboxylic acid or an ester thereof, e.g. acetic acid and ethyl acetate, and in an ether, e.g. diethyl ether, tetrahydrofuran or dioxan.

To increase the solubility in particular of the salt-like reducing agent in the reaction mixture, it is possible to add water to the reaction mixture, as required. The reaction is normally carried out in the temperature range from about $-20°$ to $100°$ C., although it can also be carried out at lower temperatures if highly reactive activators are employed.

In a compound of the formula II, a replaceable group X, e.g. halogen such as chlorine, bromine or iodine, is converted into the

group with a compound which introduces the

group, e.g. ammonia, or an alkali amide, e.g. lithium or sodium amide, a lower alkylamine, e.g. methylamine, a di-lower alkylamine, an acid amide, wherein one hydrogen atom of the amide group is replaced by an alkali metal, e.g. lithium, e.g. $R^a-CO-NR_3Li$.

The reaction of a compound of the formula II, wherein X is halogen, e.g. cholrine, with a compound which introduces the

group, e.g. with ammonia, takes place preferably in the presence of a catalyst, e.g. copper(I) oxide or copper(II) oxide, copper(I) or cooper(II) chloride or copper sulfate. The reaction is conducted in a concentrated aqueous ammonia solution or preferably in liquid ammonia, while keeping the reaction conditions described in Houben-Weyl, Methoden der Organischen Chemie (hereinafter referred to as "Houben-Weyl"), Vol. XI/1 "Nitrogen Compounds", pp. 63–67, e.g. elevated temperature above $100°$ C. and under elevated pressure.

The reaction of a compound of the formula II, wherein X is a halogen, e.g. chlorine, is preferably carried out with an alkali metal amide, e.g. lithium or potassium amide. The amide is conveniently added in the form of a suspension.

The preferred solvent is benzene or toluene and the reaction is carried out in an inert gas atmosphere, e.g. under nitrogen. The reaction is most conveniently carried out at elevated temperature, e.g. at the boiling temperature of the reaction mixture, in accordance with the reaction conditions described in Houben-Weyl, Vol. X/1 "Nitrogen Compounds", on pages 74–79, for aromatic halogen compounds.

In a compound of the formula II, a derived carboxyl group X, e.g. carbamoyl or azidocarbonyl, can be converted into the amino group under the conditions known for degradation reactions according to Hofmann (carbamoyl) or Curtius (azidocarbonyl).

The conversion according to Hofmann of the carbamoyl compound of the formula II with free halogen, e.g. bromine, into the amino compound of the formula I, is carried out under alkaline conditions. The conversion of the azidocarbonyl (carboxamide) compound of the formula II into the amino compound of the formula I according to Curtius is carried out at elevated temperature with decomposition of the azidocarbonyl group.

After the rearrangement, saponification is carried out under acid conditions, e.g. in dilute sulfuric acid.

The reaction conditions for the Hofmann and Curtius degradation are described in the article by P. A. Smith in Org. Reactions 3, 363 (1946).

Protected amino groups from which the protective group can be split off and replaced by hydrogen are described e.g. in "Protective Groups in Organic Chemistry", Plenum Press, London and New York, 1973, in "The Peptides", Vol. I, Schröder and Lubke, Academic Press, London and New York, 1965, and in Houben-Weyl, Vol. 15/1, Georg Thieme Verlag Stuttgart, 1974.

Preferred protective groups are groups which can be removed by acidolysis, for example lower alkoxycarbonyl, e.g. tert-butoxycarbonyl (BOC) or 2-halo-lower alkoxycarbonyl, e.g. 2-iodoethoxycarbonyl or 2,2,2-trichloroethoxycarbonyl.

It is also possible, however, to use amino protective groups which can be split off reductively or, under mild conditions, with a base, e.g. in particular the benzyloxycarbonyl group or a benzylcarbonyl group, wherein the phenyl radical is substituted by halogen atoms, nitro groups and/or lower alkoxy groups, e.g. the p-chloro-, p-nitro- or p-methoxybenzyloxycarbonyl group.

The removal of the protective group is effected in the conventionally known manner. The acid hydrolysis (acidolysis) is carried out e.g. with trifluoroacetic acid. The groups which can be split off reductively, especially those which contain benzyl radicals, are preferably removed by hydrogenolysis, e.g. by palladium catalysed hydrogenation.

Process (b)

In a compound of the formula III, the leaving groups $Y_1$ and $Y_2$ are each independently e.g. hydroxy, halogen, e.g. chlorine, bromine or iodine, lower alkoxy, silyloxy or sulfonyloxy.

Lower alkoxy $Y_1$ or $Y_2$ is for example methoxy, ethoxy, n-propoxy, branched lower alkoxy, e.g. tert-butoxy, or substituted lower alkoxy, e.g. benzyloxy, 4-nitrobenzyloxy or diphenylmethoxy.

Silyloxy $Y_1$ or $Y_2$ is for example tri-lower alkylsilyloxy such as trimethylsilyloxy.

Sulfonyloxy $Y_1$ or $Y_2$ is for example lower alkanesulfonyloxy such as methanesulfonyloxy, benzenesulfonyloxy or p-toluenesulfonyloxy.

A compound which introduces the

group is for example an alkali metal amide, e.g. sodium amide or potassium amide, ammonia ($R_1$=hydrogen), a lower alkylamine, e.g. methylamine ($R_1$=lower alkyl), a carbamide, e.g. urea or 1,3-dimethylurea, or a lower alkanecarboxamide, e.g. formamide, N-methylformamide, acetamide or N-methylacetamide.

The reaction with a compound which introduces the

group, e.g. with ammonia or methylamine, can be carried out stepwise. For example, it is possible to obtain first a compound of the formula III, wherein one of the leaving groups $Y_1$ or $Y_2$ is replaced by —NH—$R_1$. Such a compound, e.g. the monoamide, can be isolated or converted into a compound of the formula I in situ by removal of $HY_1$ or $HY_2$.

A compound of the formula III, wherein e.g. $Y_1$ or $Y_2$ is hydroxy, can be converted first into its anhydride, e.g. at elevated temperature, or by dehydration with a conventional dehydrating agent, e.g. acetic anhydride or acetyl chloride. This anhydride can be isolated or converted into a compound in which one of the leaving groups $Y_1$ or $Y_2$ is replaced by —NH—$R_1$, the conversion being carried out in situ by reaction with a compound which introduces the group

e.g. ammonia or methylamine. Such a monoamide can subsequently be cyclised to a compound of the formula I by splitting off water.

During the cyclisation, a total of 2 moles of $HY_1$ or $HY_2$, e.g. HCl or HBr, are set free and are bound for example by an excess of the

donor, e.g. ammonia or methylamine.

It is preferred to carry out the reaction in an inert polar solvent, e.g. in benzene, toluene, xylene, methylene chloride, ether or methanol or in a mixture thereof. The reaction temperature is in the range from −20° to about +80° C., preferably from 0° to about 30° C. If an acid halide of the formula III, e.g. the acid dichloride, is reacted with ammonia, the reaction is preferably carried out with cooling, for example below 0° C.

Process (c)

The introduction of the —CH$_2$— group into a compound of the formula IV is effected by addition of a methylene group to the olefinic double bond of the maleimide to form a cyclopropyl ring. The —CH$_2$— group can be introduced for example by reaction with a sulfur ylide compound, e.g. a (dialkylamino)methysulfoxonium methylide, e.g. (dimethylamino)- or (diethylamino)methylsulfoxonium methylide, or a dialkylsulfoxonium methylide, e.g. dimethyl- or diethylsulfoxonium methylide, or with dihalomethane, e.g. dichloro, dibromo- or diiodomethane, in the presence of a zinc-/copper catalyst.

The sulfur ylide compound is conveniently prepared in a solvent (q.v. C. R. Johnson and P. E. Rogers, J. Org. Chem. Vol. 38, No. 10, 1793-1797, 1978, preparation of (dimethylamino)methylsulfoxonium methylide in dimethylsulfoxide, and P. T. Izzo, J. Org. Chem. 1963, pp. 1713-1715, preparation of dimethylsulfonium methylide in tetrahydrofuran) and then reacted, optionally in situ, with the compound of the formula IV. The reaction is carried out normally at room temperature, with cooling, e.g. to −20° C., or with gentle heating, e.g. to 40° C. The dialkylsulfinamide formed during the subsequent reaction is removed in the course of the aqueous working up.

The reaction of the maleimide of the formula IV with dihalometane is carried out under the known reaction conditions for the SimmonsSmith reaction (q.v. Houben-Weyl, Vol. 4/3, pp. 115-116). The compound of the formula IV is reacted with the appropriate dihalomethane, e.g. diiodomethane, in an inert solvent, e.g. in a hydrocarbon, e.g. benzene, an ether, e.g. diethyl ether, or in an ester, e.g. ethyl acetate, in the presence of a zinc/copper catalyst (prepared e.g. from zinc dust and copper(II) acetate in glacial acid), and the reaction product is subsequently washed with ether. The reaction is preferably carried out at room temperature or with gentle heating, e.g. at a temperature above 30° C.

The methylene group —$CH_2$— can also be introduced with diazomethane, which can be inserted in the maleimide first to form a pyrazoline ring. For example, an ethereal solution of diazomethane which has been prepared in situ (q.v. Houben-Weyl, Vol. X/4, p. 473 et seq.) is combined with an ethereal solution of the maleimide of the formula IV, whereupon the addition reaction takes place spontaneously or with gentle heating. The elimination of nitrogen from the pyrazoline ring can be effected at room temperature or with heating, e.g. in the temperature range up to the boiling point of the reaction mixture. The elimination of nitrogen at room temperature can be speeded up by the addition of a catalyst, e.g. platinum or copper powder.

Diazomethane can also be decomposed in an inert solvent, e.g. in hexane or in ether, whereupon the free methylene reacts with the maleimide compound of the formula IV to form direct the cyclopropane ring. The decomposition of diazomethane is preferably carried out catalytically, e.g. in the presence of a noble metal in finely divided form, e.g. copper, or of a metal salt, e.g. copper(I) chloride or copper(II) sulfate.

In compounds of the formula IV, wherein $R_1$ is hydrogen, the imido function is protected by an amino protective group before the reaction with diazomethane. Suitable amino protective groups are described above under process (a).

Instead of —$CH_2$—, it is also possible to introduce $C(Hal)_2$, $C(Br)_2$ or $C(I)_2$, which adds on to the olefinic double bond of the maleimide of the formula IV of form a dihalo-substituted cyclopropane ring. The dihalo compound can then be converted by reduction into a compound of the formula I.

Subsequent operations

Within the scope of their definitions, the substituents $R_1$, $R_2$ and $R_3$ in a compound of the formula I can be converted into other substituents $R_1$, $R_2$ and $R_3$. Accordingly, a free amino group can be converted into an acylamino group in which $R_2$ is acyl and $R_3$ is hydrogen or lower alkyl. These subsequent operations are carried out in a manner known per se, for example as follows:

Acylation of the amino group at the phenyl ring

If in a compound of the formula I $R_2$ and $R_3$ are hydrogen and $R_1$ is a hydrocarbon radical, the free amino group at the phenyl ring can be substituted in a manner known per se by an acyl group $R_2$ or by a lower alkyl radical $R_3$. If $R_1$ is hydrogen, the imido group must be protected by one of the amino protective groups mentioned above. This substitution can be effected e.g. by acylation with a suitable acylating agent which introduces the corresponding acyl radical $R_2$. The amino group at the phenyl ring is in the free form or in reactive, i.e. acylatable, protected, e.g. silylated, form.

If the amino group at the phenyl ring in a compound of the formula I is substituted by an acyl radical $R^b$—$SO_2$—, the acylating agent employed is e.g. the corresponding sulfonic acid or a reactive functional derivative thereof, in particular an anhydride thereof, e.g. a mixed anhydride. A mixed anhydride of a sulfonic acid is formed e.g. by condensation with an inorganic acid, for example a hydrohalic acid, e.g. hydrochloric acid, and is e.g. the corresponding sulfonic acid halide, e.g. the sulfonic acid chloride or bromide.

If the amino group at the phenyl ring is substituted by an acyl group $R^b$—CO—, the acylating agent employed is e.g. the corresponding carboxylic acid itself or a reactive functional derivative thereof.

A reactive, i.e. carboxamide function forming, functional derivative of a carboxylic acid is an anhydride of this carboxylic acid, preferably a mixed anhydride. A mixed anhydride is formed e.g. by condensation with another acid, e.g. an inorganic acid such as a hydrohalic acid, and is for example the corresponding carboxylic acid halide, e.g. the carboxylic acid chloride or bromide. A reactive functional derivative of a carboxylic acid of the formula III is furthermore formed by condensation with a lower alkyl hemiester of carbonic acid, e.g. the ethyl or isobutyl hemiester of carbonic acid.

If the amino group at the phenyl ring is substituted by an acyl radical R having the meanings $R^b$—O—CO—, $(R^b)(R^b)N$—CO— or $(R^b)(R^b)N$—$SO_2$, the acylating agent employed is a reactive derivative of the corresponding carbonic acid hemiester or of the corresponding carbamic acid or amidosulfonic acid. Examples of such reactive derivatives are anhydrides, e.g. mixed anhydrides, which are formed by condensation with inorganic acids such as hydrohalic acids, e.g. hydrochloric acid, or, if a carbamic acid is used, are also inner anhydrides, e.g. cyanates.

The acylation reactions are preferably carried out in the presence of a suitable acid acceptor, for example of a suitable organic base. A suitable organic base is e.g. an amine, e.g. a tertiary amine such as a tri-lower alkylamine, e.g. trimethylamine or triethylamine, a cyclic tertiary amine such as N-methylmorpholine, a bicyclic amidine, e.g. a diazabicycloalkene such as 1,5-diazabicyclo[4.3.0]non-5-ene or 1,5-diazabicyclo[5.4.0]undec-5-ene (DBU), or is, for example, a base of the pyridine type, e.g. pyridine. A suitable acid acceptor is also an inorganic base, for example an alkali metal hydroxide or alkaline earth metal hydroxide, e.g. sodium, potassium or calcium hydroxide.

The acylation reactions are preferably carried out in an inert, preferably anhydrous, solvent or mixture of solvents, for example in dimethylformamide, methylene chloride, carbon tetrachloride, chlorobenzene, acetone, tetrahydrofuran, ethyl acetate or acetonitrile, or in mixtures thereof, if desired at low or elevated temperature, e.g. in the temperature range from about −40° to +100° C., preferably from about −10° to +50° C., and optionally in an inert gas atmosphere, e.g. under nitrogen.

The acylation of the free amino group at the phenyl ring can be carried out both in the final product of the formula I and in the intermediates of the formulae II, III and IV by the method described above.

Substitution of the amino group at the phenyl ring by sulfo

If in a compound of the formula I $R_2$ and $R_3$ are hydrogen and $R_1$ is a hydrocarbon radical, the free amino group at the phenyl ring can be substituted by sulfo in a manner known per se. This substitution can be effected e.g. by reacting an aminophenyl compound of the formula I with triethylamine in a sulfur trioxide complex. To prevent the imido function ($R_1$=hydrogen) from being substituted by sulfo, it must be protected by one of the amino protective groups mentioned above.

Alkylation of the amino group at the phenyl ring

If in a compound of the formula I $R_2$ and $R_3$ are hydrogen, the free amino group at the phenyl ring can be substituted by two equivalents of a suitable alkylating agent which introduces the lower alkyl radical, e.g. an alkyl halide such as methyl bromide, to give the di-lower alkyl-substituted amino group ($R_2$ and $R_3$=lower alkyl).

The free amino group at the phenyl ring can also be protected by one of the above mentioned customary amino protective groups, e.g. by tert-butoxycarbonyl, and, after subsequent metalation of the so protected amino group with a suitable metalating reagent, alkylated with a reactive alkylating agent corresponding to the lower alkyl radical $R_2$ and $R_3$.

After removal of the amino protective groups, there is obtained a monoalkyl-substituted amino group ($R_2$=H and $R_3$=lower alkyl or $R_2$=lower alkyl and $R_3$=H).

Examples of suitable metalating reagents are lithium diisopropylamide or butyllithium. A reactive compound corresponding to the radical $R_3$ is, for example, a compound of the formula $R_2$—X or $R_3$—X, wherein X is a leaving group, for example a halogen atom, e.g. chlorine, bromine or iodine, or is a sulfonyloxy group such as mesyloxy or tosyloxy.

If it is not desired to alkylate the imido function ($R_1$=hydrogen), then this group may be protected by one of the customary protective groups mentioned above.

The separation of mixtures of diastereoisomers obtained by the process of the invention into optically pure antipodes is effected in a manner known per se, for example by physical or chemical methods, for example by functional crystallisation. It is also possible, however, to use chromatographic methods, e.g. solidliquid chromatography. Volatile mixtures of diastereoisomers can also be separated by distillation or by chromatography.

The separation of racemates obtained by the process of the invention into optically pure antipodes is affected in a manner known per se, e.g. by chromatography on optically active adsorption layers. The racemates can also be dissolved in optically active solvents and the more sparingly soluble optical antipode can be crystallised from the solution so obtained. Further, use is also made of the different reactivity of the optical antipodes towards biological material such as microorganisms or isolated enzymes, or the racemates are dissolved and an optical antipode is crystallised by inoculating the solution with a small amount of an optically active product which is obtained by the above methods.

Instead of the final compound of the formula I itself, it is also possible to resolve a precursor obtained in racemic form, for example an intermediate of the formula III, wherein $Y_1$ or $Y_2$ is hydroxy, into optically pure antipodes, and then to convert the optically pure antipode of this precursor into an optically pure antipode of the final compound of the formula I. The reactions according to processes (a), (b) and (c) do not in general change the configuration of the 1- and 5-C-atom. The addition of methylene to the olefinic double bond of the maleimide of the formula IV according to process (c) proceeds in general stereospecifically (cis-addition).

Acid addition salts are obtained in conventional manner, e.g. by treatment with an acid or a suitable anion exchanger.

The process also comprises those embodiments in which compounds obtained as intermediates are used as starting materials and the remaining process steps are carried out therewith, or the process is interrupted at any stage; further, starting materials may be used in the form of derivatives or formed during the reaction.

The starting materials employed and the reaction conditions chosen are preferably those which result in the compounds described above as being especially preferred.

Starting materials

The starting materials employed in the process for the preparation of the compounds of formula I are known or, if they are novel, can be obtained in a manner known per se.

Starting materials of the formula II, wherein X is halogen or nitro, are described in German Offenlegungsschrift No. 27 40 562.

Starting materials of the formula II, wherein X is e.g. nitroso or hydroxylamino, or a replaceable group such as carbamoyl or azidocarbonyl, or is protected amino, are novel and are also an object of the present invention. They can be prepared e.g. in a manner known per se by cyclising a compound of the formula

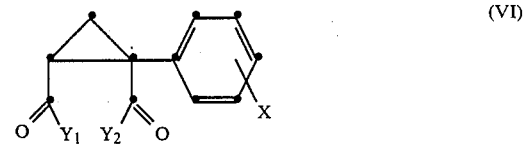

(VI)

wherein $Y_1$ and $Y_2$ are leaving groups and $X'$ is nitroso or hydroxylamino, carboxyl or protected amino, or a salt thereof, by reaction with a compound which introduces the group —NH—$R_1$ and, in a resultant compound, converting the carboxyl group into a replaceable group, e.g. carbamoyl or azidocarbonyl, and/or, if desired, converting a compound of the formula II into another compound of the formula II and/or converting a resultant salt into the free compound or into another salt, and/or converting a resultant free compound into a salt and/or separating a mixture of isomers into the individual isomers.

The process can be carried out in accordance with the reaction conditions described under process (b). The conversion of the carboxyl group X' in a compound of the formula II into an azidocarbonyl or carbamoyl group can be carried out in accordance with the methods for obtaining derivatives of aromatic carboxyl groups described in Organikum, VEB Deutscher Verlag der Wissenschaften, latest edition.

Starting materials of the formula III are novel and also consistute an object of the invention. They can be obtained for example in a manner known per se by reacting a compound of the formula

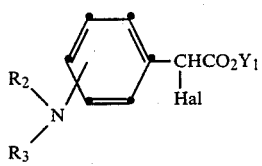
(VII)

wherein $R_2$ and $R_3$ are as defined for formula I and $Y_1$ is as defined for formula III and Hal is chlorine or bromine, with an acrylic acid derivative of the formula $$HC=CHCO_2Y_2 \quad (VIII)$$

wherein $Y_2$ is as defined for formula III, and, if desired, separating a resultant mixture of isomers into the individual isomers.

The preparation of compounds of the formula III can be carried out as described by L. L. McCoy in J.A.C.S., 1958, 80, 6568 and 1962, 84, 2246, and in J. Org. Chem. 1960, 25, 2078.

Starting materials of the formula IV, wherein $R_1$ is hydrogen and one of $R_2$ and $R_3$ is acetyl and the other is hydrogen, and the preparation thereof, are described in published Japanese patent application No. 71-35,259, see also CAS Reg. No. 34648-97-0.

Starting materials of the formula IV, wherein $R_1$ is as defined for formula I, $R_2$ is hydrogen, lower alkyl or sulfo, and $R_3$ is hydrogen or lower alkyl, are prepared e.g. by reacting a maleimide compound of the formula

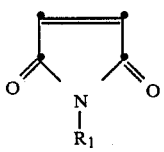
(IX)

wherein $R_1$ is as defined for formula I, with a diazonium salt of the formula

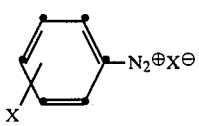
(X)

wherein X is as defined for formula II and Hal is chlorine or bromine, and, in a compound so obtained, converting X into the group of the partial formula $-NR_2(R_3)$, and/or, if desired, converting a resultant salt into the free compound or into another salt, and/or converting a resultant free compound into a salt.

The reaction of a compound of the formula IX with a diazonium salt of the formula IX is carried out according to Ch. S. Rondestvedt and O. Vogel in JACS, 77, 2313-2315 (1955). The conversion of X into the group of the partial formula $-NR_2(R_3)$ is described above under process (a) and in the section "Subsequent operations".

Compounds of the formula VI can be prepared in the same way as compounds of the formula III in accordance with L. L. McCoy in JACS, 1958, 80, 6258 and 1962, 84, 2246, and in JOCS, 1960, 25, 2078.

Starting materials of the formulae VII, VIII, IX and X are known or, if they are novel, can be prepared in a manner known per se.

The invention is illustrated by the following Examples.

Abbreviations m.p. = melting point
b.p. = boiling point

EXAMPLE 1

1-(4-Aminophenyl)-3-azabicyclo[3.1.0]hexan-2,4-dione

To a solution of 25.9 g of 1-(4-nitrophenyl)-3-azabicyclo[3.1.0]hexane-2,4-dione (preparation as described in DE-OS 2 740 562) in 700 ml of ethanol are added 1.4 g of 5% palladium/carbon catalyst. Hydrogenation is carried out under normal pressure and at room temperature with hydrogen. When the absorption of hydrogen is complete (theoretical amount: 7500 ml), the reaction mixture is diluted with 1 ml of ethanol and concentrated after removal of the catalyst. The product so obtained is recrystallised from ethanol, affording the title compound with m.p. 183°-185° C.

EXAMPLE 2

(a)

1-(3-Aminophenyl)-3-azabicyclo[3.1.0]hexane-2,4-dione

Following the procedure of Example 1, 600 mg of 1-(3-nitrophenyl)-3-azabicyclo[3.1.0]hexane-2,4-dione are dissolved in 30 ml of ethanol and reduction is carried out with hydrogen in the presence of 60 mg of 5% palladium/carbon. When the hydrogenation is complete, the mixture is diluted with ethanol and the catalyst is removed by filtration over HYFLO-Super-Cel ®. The solvent is stripped off in vacuo and the residue is recrystallised from a mixture of ethyl acetate/petroleum ether, affording the title compound in the form of pale pink crystals with m.p. 135°-137° C. and an Rf value of 0.47 on thin-layer silica gel plates in the system methylene chloride/methanol (10:1), or 0.52 in methylene chloride/methanol/glacial acetic acid (40:5:1).

Preparation of the starting material (b) Ethyl 2-chloro-(3-nitrophenyl)acetate

A mixture of 97 g of ethyl 3-nitromandelate and 69 ml of thionyl chloride is stirred overnight at room temperature. Then a few drops of pyridine are added. After the evolution of gas has ceased, the mixture is stirred for about 2 hours at 100° C. Excess thionyl chloride is evaporated off in a water jet vacuum and the reaction mixture is distilled in a high vacuum. The title compound (b) is obtained in the form of a yellow oil with b.p. 134° C. at 0.06 mbar and with an Rf value of 0.5 on thin-layer silica gel plates in a methylene chloride system.

(c) Diethyl 1-(3-nitrophenyl)-1,2-cyclopropanedicarboxylate

With stirring and under nitrogen, a mixture of 68.2 g of ethyl 1-chloro-1-(3-nitrophenyl)acetate and 30.5 ml of ethyl acrylate is slowly added dropwise at 50° C. to a suspension of 12.3 g of sodium hydride (55–60% in paraffin oil) in 67 ml of tuolene. To initiate and speed up the reaction, a few drops of a 1:1 mixture of alcohol/ether are added to the reaction mixture from time to time. When the reaction is complete, 350 ml of water are cautiously added dropwise. After two extractions with ether, the organic phases are washed twice with water and once with a dilute solution of sodium chloride, dried over magnesium sulfate and filtered. The solution is evaporated to dryness and the residue is chromatographed over 1 kg of silica gel (0.063 to 0.280 mm). The title compound (c) is obtained in the form of a brown oil with an Rf value of 0.15 on silica gel thin-layer plates in a methylene chloride system.

(d) 1-(3-Nitrophenyl)-1,2-cyclopropanedicarboxylic acid 14.2 g of diethyl 1-(3-nitrophenyl)-1,2-cyclopropanedicarboxylate are dissolved in 150 ml of methanol and to this solution are added 100 ml of 1N sodium hydroxide solution. The mixture is stirred overnight and the solvent is then removed from the dark brown solution. The reaction mixture is extracted twice with ether after cooling to 0° C. and adding 50 ml of 2N hydrochloric acid. The ethereal phases are washed repeatedly with a small amount of water, dried over magnesium sulfate, filtered and concentrated. The crystals so obtained are recrystallised from boiling ethyl acetate by adding petroleum ether. The title compound (d) is obtained in the form of pale beige-coloured crystals with m.p. 167°–170° C. and Rf=0.2 on thin-layer silica gel plates in the system methylene chloride/methanol/glacial acetic acid (40:5:1:).

(e) 1-(3-Nitrophenyl)-3-azabicyclo[3.1.0]hexane-2,4-dione

A mixture of 9.8 g of 1-(3-nitrophenyl)-1,2-cyclopropanedicarboxylic acid and 4.9 g of urea in 250 ml of xylene (mixture of isomers) is stirred for about 16 hours at a bath temperature of about 150° C. The xylene is then evaporated off in vacuo and the residue is partitioned between ethyl acetate and water. The organic phases are combined, dried over MgSO4, filtered, and concentrated in vacuo. Recrystallisation from ethyl acetate/petroleum ether gives the title compound (e) in the form of pale yellow crystals with m.p. 173°–174° C. and Rf=0.3 on thin-layer silica gel plates in the system hexane/ethyl acetate (4:6).

EXAMPLE 3

(a) 1-(4-Aminophenyl)-3-methyl-3-azabicyclo[3.1.0]hexane-2,4-dione

A solution of 1.5 g of 3-methyl-1-(4-nitrophenyl)-3-azabicyclo[3.1.0]hexane-2,4-dione in 50 ml of ethanol is hydrogenated in the presence of 0.1 g of 5% palladium on carbon. When the hydrogenation is complete, the catalyst is removed and the filtrate is concentrated and the residue is recrystallised from ethyl acetate/petroleum ether. The title compound is obtained in the form of pale pink crystals with m.p. 137°–139° C. and Rf=0.47 on thin-layer silica gel plates in the system methylene chloride/methanol (15:1).

Preparation of the starting material

(b) 3-Methyl-1-(4-nitrophenyl)-3-azabicyclo[3.1.0]hexane-2,4-dione 2.32 g of 1-(4-nitrophenyl)-3-azabicyclo[3.1.0]hexane-2,4-dione are dissolved in 25 ml of dimethylformamide and 0.3 g of sodium hydride (pract. Fluka) is added under nitrogen.

After it has been stirred for 30 minutes at room temperature, the mixture is cooled to 0° C. and then 0.93 ml of methyl iodide in 5 ml of dimethylformamide is added. The reaction mixture is stirred for another 5 hours and then excess sodium hydride is destroyed with methanol. The solvent is then stripped off in vacuo and the residue is partitioned between ethyl acetate/water and a concentrated solution of sodium chloride. The aqueous phases are washed once with ethyl acetate. The organic phases are dried over magnesium sulfate, filtered and concentrated. Recrystallisation of the residue from ethyl acetate/petroleum ether yields the title compound (b) in the form of colourless crystals with m.p. 148°–150° C. and Rf=0.7 on thin-layer silica gel plates in the system methylene chloride/methanol/glacial acetic acid (40:5:1).

EXAMPLE 4

3-Ethyl-1-(4-aminophenyl)-3-azabicyclo[3.1.0]hexane-2,4.dione

Following the procedure of Example 3, a solution of 4.1 g of 3-ethyl-1-(4-nitrophenyl)-3-azabicyclo[3.1.0.]hexane-2,4-dione in 120 ml of ethanol is hydrogenated in the presence of 0.2 g of 5% palladium on carbon and worked up, affording the title compound which melts at 116°–118° C. after recrystallisation from ethyl acetate/petroleum ether. The starting material is synthesised in accordance with the procedure described in Example 3, starting from 4.6 g of 1-(4-nitrophenyl)-3-azabicyclo[3.1.0]hexane-2,4-dione, 0.72 g of sodium hydride (pract. Fluka) and 2 ml of methyl iodide. Melting point: 155°–157° C. (after recrystallisation from ethyl acetate/petroleum ether).

EXAMPLE 5

1-(4-Aminophenyl)-3-n-propyl-3-azabicyclo[3.1.0]hexane-2,4-dione

Following the procedure of Example 3, a solution of 3.4 g of 1-nitrophenyl)-3-n-propyl-3-azabicyclo[3.1.0]hexane-2,4-dione in 120 ml of ethanol are hydrogenated in the presence of 0.2 g of palladium on carbon and worked up, affording the title compound which melts at 114°–115° C. after recrystallisation from ethyl acetate/petroleum ether.

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 2.44 ml of propyl iodide. Melting point: 97° C. (recrystallisation from ether).

EXAMPLE 6

1-(4-Aminophenyl)-3-isopropyl-3-azabicyclo[3.1.0]hexane-2,4-dione

Following the procedure of Example 3, a solution of 3-isopropyl-1-(4-nitrophenyl)-3-azabicyclo[3.1.0]hexane-2,4-dione in 100 ml of ethanol is hydrogenated in the presence of 0.17 g of 5% palladium on carbon and worked up, affording the title compound which melts at 160°–163° C. after recrystallisation from ethyl acetate/petroleum ether.

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 2.5 ml of isopropyl iodide. Melding point: 115°–118° (recrystallisation from ethylacetate/petroleum ether).

EXAMPLE 7

1-(Aminophenyl)-3-n-butyl-3-azabicyclo[3.1.0]hexane-2,4-dione

Following the procedure of Example 3, a solution of 4 g of 3-n-butyl-1-(4-nitrophenyl)-3-azabicyclo[3.1.0]hexane-2,4-dione in 120 ml of ethanol is hydrogenated in the presence of 0.2 g of 5% palladium on carbon and worked up, affording the title compound which melts at 95°–98° C. after recrystallisation from ether/petroleum ether.

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 2.9 ml of n-butyl iodide. The product is a yellow oil with $R_6=0.2$ on thin layer silica gel plates in the system hexane/ethyl acetate (2.1).

EXAMPLE 8

1-(4-Aminophenyl)-3-isobutyl-3-azabicyclo[3.1.0]hexane-2,4-dione

Following the procedure of Example 3, a solution of 0.55 g of 3-isobutyl-1-(4-nitrophenyl)-3-azabicyclo[3.1.0]hexane-2,4-dione in 25 ml of ethanol is hydrogenated in the presence of 0.1 g of 5% palladium on carbon and worked up, affording the title compound which melts at 115°–117° C. after recrystallisation from ether/petroleum ether.

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 3.5 ml of isobutyl iodide. Melting point: 100°–101° C. (recrystallisation from ethyl acetate/petroleum ether).

EXAMPLE 9

1-(4-Aminophenyl)-3-n-pentyl-3-azabicyclo[3.1.0]hexane-2,4-dione

Following the procedure of Example 3, a solution of 5.3 g of 1-(4-nitrophenyl)-3-n-pentyl-3-azabicyclo[3.1.0]hexane-2,4-dione in 150 ml of ethanol is hydrogenated in the presence of 0.25 g of 5% palladium on carbon and worked up, affording the title compound which melts at 113°–115° C. after recrystallisation from ethyl acetate/petroleum ether.

The starting material is synthesised in accordance with Example 3, starting from 4.6 of 1-(4-nitrophenyl)-3-azabicyclo[3.1.0]hexane-2,4-dione, 0.72 g of sodium hydride (pract. Fluka) and 3.3 ml of pentyl iodide. The product is a yellow oil with Rf=0.52 on thin-layer silica gel plates in the system hexane/ethyl acetate (4:6).

EXAMPLE 10

1-(4-Aminophenyl)-3-neopentyl-3-azabicyclo[3.1.0]hexane-2,4-dione

Following the procedure of Example 3, a solution of 0.85 g of 3-n-pentyl-1-(4-nitrophenyl)-3-azabicyclo[3.1.0]hexane-2,4-dione in 30 ml of ethanol is hydrogenated in the presence of 0.1 g of 5% palladium on carbon and worked up, affording the title compound which melts at 140°–143° C. after recrystallisation from ether/petroleum ether.

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 3.3 ml of neopentyl iodide. Melting point: 118°–119° C. (recrystallisation from ether/petroleum ether).

EXAMPLE 11

1-(4-Aminophenyl)-3-n-heptyl-3-azabicyclo[3.1.0]hexane-2,4-dione

Following the procedure of Example3, a solution of 5 g of 3-n-heptyl-1-(4-nitrophenyl)-3-azabicyclo[3.1.0]hexane-2,4-dione in 100 ml of ethanol is hydrogenated in the presence of 0.3 g of 5% palladium on carbon and worked up, affording the title compound which melts at 78°–79° C. after recrystallisation from ether/petroleum ether.

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 3.9 ml of heptyl bromide. The product is a yellow oil with Rf=0.55 on thin-layer silica gel plates in the system hexane/ethyl acetate (4:6).

EXAMPLE 12

1-(4-Aminophenyl)-3-cyclohexylmethyl-3-azabicyclo[3.1.0]hexane-2,4-dione

Following the procedure of Example 3, a solution of 0.5 g of 3-cyclohexylmethyl-1-(4-nitrophenyl)-3-azabicyclo[3.1.0]hexane-2,4-dione in 30 ml of ethanol is hydrogenated in the presence of 0.1 g of 5% palladium on carbon and the reaction mixture is worked up, affording the title compound which melts at 125°–126° C. after recrystallisation from ethyl acetate/petroleum ether.

The starting material is synthesised in accordance with Example 3, starting from 2.3 g of 1-(4-nitrophenyl)-3-azabicyclo[3.1.0]hexane-2,4-dione, 0.36 g of sodium hydride (pract. Fluka) and 1.7 g of cyclohexylmethyl chloride. Melting point: 125°–126° C. (recrystallisation from ether/petroleum ether).

EXAMPLE 13

1-(4-Aminophenyl)-3benzyl-3-azabicyclo[3.1.0]hexane-2,4-dione

Following the procedure of Example 3, a solution of 2.0 g of 3-benzyl-1-(4-nitrophenyl)-3-azabicyclo[3.1.0]hexane-2,4-dione in 100 ml of ethanol is hydrogenated in the presence of 0.2 g of 5% palladium on carbon and worked up, affording the title compound which melts at 154°–155° C. after recrystallsation from ethanol.

The starting material is synthesised in accordance with Example 3, starting from 2.3 g of 1-(4-nitrophenyl)-3-azabicyclo[3.1.0]hexane-2,4-dione, 0.3 g of sodium hydride (pract. Fluka) and 1.2 ml of benzyl chloride. Melting point: 147°–149° C. (recrystallisation from ethyl acetate).

EXAMPLE 14

(a)
1-(4-Aminophenyl)-3-azabicyclo[3.1.0]hexane-2,4-dione

In a glass bomb tube, 2.3 g of 1-(4-aminophenyl)-1,2-cyclopropanedicarboxylic acid are stirred in 80 ml of approx. 1N methanolic ammonia solution for 7 days at 100° C. The reaction mixture is evaporated to dryness and the residue is chromatographed over silica gel with hexane/ethyl acetate (4:6). Recrystallisation from ethanol affords white crystals of the title compound, which is identical with the title compound of Example 1.

Preparation of the starting material:

(b) 1-(4-Aminophenyl)-1,2-cyclopropanedicarboxylic acid 20 g of 1-(4-nitrophenyl)-1,2-cyclopropanedicarboxylic acid are dissolved in 200 ml of ethanol and the solution is hydrogenated in the presence of 5% palladium on carbon. The suspension so obtained is diluted with methanol and the precipitated product is dissolved by addition of 1 equivalent of methanolic hydrochloric acid. A part of the solvent is stripped off in vacuo, then 1 equivalent of 2N sodium hydroxide solution is added and the mixture is evaporated to dryness. The residue is crystallised from water and dried in vacuo over KOH pellets at 60° C. The title compound (b) is obtained in the form of light brown crystals with a melting point above 230° C. and Rf=0.55 on thin-layer silica gel plates in the system methylene chloride/glacial acetic acid (20:10:2).

EXAMPLE 15

1-(4-Aminophenyl)-3-methyl-3-azabicyclo[3.1.0]hexane-2,4-dione

A mixture of 220 mg of 1-(4-aminophenyl)-1,2-cyclopropanedicarboxylic acid, 10 ml of methanol and 0.26 ml of methylamine (40%) is stirred in a glass bomb tube for 7 days at 100° C. The mixture is concentrated in vacuo and the residue is chromatographed over a column of silica gel with a 4:6 mixture of hexane/ethyl acetate. Recrystallisation from ethyl acetate/petroleum ether affords yellow crystals of the title compound, which is identical with the title compound of Example 3(a).

EXAMPLE 16

(a)
1-(4-Aminophenyl)-3-n-propyl-3-azabicyclo[3.1.0]hexane-2,4-dione

A mixture of 52 mg of 1-(4-aminophenyl)-1,2-cyclopropanedicarboxylic acid 2-N-propylamide and 5 ml of xylene (mixture of isomers) is stirred for 24 hours at 150° C. The mixture is concentrated and the residue is taken up in ethyl acetate. The solution is filtered over Hyflo-Supercel ® and crystallised by addition of petroleum ether, affording the title compound, which is identical with the title compound of Example 5.

Preparation of the starting material:
1-(4-Nitrophenyl)-1,2-cyclopropanedicarboxylic acid 2-N-propylamide 2.1 g of N,N'-dicyclohexylcarbodiimide are added to a solution of 2.5 g of 1-(4-nitrophenyl)-1,2-cyclopropanedicarboxylic acid in 50 ml of tetrahydrofuran and the mixture is stirred for 1 hour at room temperature. A solution of 0.83 ml of propylamine and 10 ml of tetrahydrofuran is then added dropwise at room temperature to the resultant suspension. The mixture is then stirred at room temperature until reaction is complete. The solvent is evaporated off, the residue is taken up in water and 1 equivalent of sodium hydroxide solution, and the precipitated urea is removed by filtration. The filtrate is acidified with 1 equivalent of hydrochloric acid and extracted twice with methylene chloride. The organic phases are washed once with water, dried over magnesium sulfate and concentrated. Recrystallisation of the residue from ethyl acetate/ether/petroleum ether affords white crystals of the title compound (b) with m.p. 154°–155° C. and Rf=0.45 on thin-layer silica gel plates in the system methylene chloride/methanol/glacial acetic acid (40:5:1).

(c) 1-(4-Aminophenyl)-1,2-cyclopropanedicarboxylic acid 2-N-propylamide

A solution of 1.5 g of 1-(4-nitrophenyl)-1,2-cyclopropanedicarboxylic acid 2-N-propylamide in 30 ml of ethanol is hydrogenated in the presence of 5% palladium on carbon. For working up, the reaction mixture is diluted with methanol in the ratio 1:1, filtered to remove the catalyst, and then concentrated. Recrystallisation from isopropanol affords pale beige-coloured crystals of the title compound (c) with m.p. 170°–172° C. (decomposition) and Rf=0.3 in thin-layer silica gel plates in the system methylene chloride/metanol/glacial acetic acid (40:5:1).

EXAMPLE 17

1-(4-Acetylaminophenyl)-3-azabicyclo[3.1.0]hexane-2,4-dione

A solution of 2.4 ml of acetic anhydride in 10 ml of tetrahydrofuran is added dropwise to a solution of 4 g of 1-(4-aminophenyl)-3-azabicyclo[3.1.0]hexane-2,4-dione and 120 mg of dimethylaminopropane in 150 ml of tetrahydrofuran, and the mixture is stirred overnight at room temperature. Then 0.5 ml of ethanol is added to the reaction mixture, which is stirred for 1 hour and filtered. The crystals so obtained are washed with tetrahydrofuran and ether, affording white crystals of the title compound with a melting point above 230° C. and Rf=0.3 in thin-layer silica gel plates in the system methylene chloride/methanol (10:1).

EXAMPLE 18

1-(4-Aminophenyl)-3-azabicyclo[3.1.0]hexane-2,4-dione 61 mg of 1-(4-acetylamino)-3-azabicyclo[3.1.0]hexane-2,4-dione are stirred for 3 hours at 100° C. in 0.5 ml of approx. 18% hydrochloric acid. The reaction mixture is cooled to 0° C. and adjusted to pH 7 with saturated aqueous bicarbonate solution. The crystalline white precipitate is isolated by filtration, washed with a small amount of cold water and recyrstallised from ethanol. The title compound so obtained is identical with the title compound of Example 1.

EXAMPLE 19

1-(4-Acetylaminophenyl)-3-methyl-3-azabicyclo[3.1.0-]hexane-2,4-dione 1.2 g of 1-(4-acetylaminophenyl)-3-azabicyclo[3.1.0-]hexane-2,4-dione, 120 mg of sodium hydride and 25 ml of N,N′-dimethylformamide are stirred, under nitrogen, for 15 minutes at 50° C. The mixture is cooled to 20° C. and then a solution of 0.32 ml of methyl iodide in 2.5 ml of dimethylformamide is slowly added dropwise. The reaction mixture is stirred for 16 hours at room temperature. Excess sodium hydride is destroyed with methanol and the reaction mixture is freed from solvent in a high vacuum. The residue is partitioned repeatedly between ethyl acetate and a dilute solution of sodium chloride. The organic phases are dried over magnesium sulfate, filtered, concentrated, and the residue is crystallised from ethyl acetate/petroleum ether. The title compound is obtained in the form of white crystals with a melting point of 183°–184° C. and with Rf=0.37 on thin-layer silica gel plates in the system methylene chloride/methanol (10:1).

EXAMPLE 20

1-(4-Aminophenyl)-3-methyl-3-azabicyclo[3.1.0]hexane-2,4-dione

A mixture of 130 mg of 1-(4-acetylaminophenyl)-3-methyl-3-azabicyclo[3.1.0]hexane-2,4-dione and 1 ml of approx. 18% hydrochloric acid is stirred for about 4 hours at 100° C. The reaction mixture is adjusted at 0° C. to pH 9–10 with saturated aqueous sodium bicarbonate solution and extracted twice with ethyl acetate. The organic phases are washed until neutral with a small amount of water and a dilute solution of sodium chloride, dried over magnesium sulfate, filtered and concentrated. Recrystallisation from ethyl acetate/petroleum ether affords the title compound which is identical with the title compound of Example 3(a).

EXAMPLE 21

1-(4-Aminophenyl)-3-methyl-3-azabicyclo[3.1.0]hexane-2,4-dione

An approx. 0.3 molar solution of diazomethane is added dropwise at 0° C. to a solution of 202 mg of 1-(4-aminophenyl)-3-azabicyclo[3.1.0]hexane-2,4-dione in 10 ml of methanol. The reaction mixture is allowed to stand for 16 hours, concentrated, and partitioned twice between ethyl acetate and water. The organic phases are dried over magnesium sulfate, filtered and concentrated. The residue is crystallised from ethyl acetate/petroleum ether, affording the title compound which is identical with the title compound of Example 3(a).

EXAMPLE 22

1-(4-Methanesulfonylaminophenyl)-3-azabicyclo[3.1.0-]hexane-2,4dione

A solution of 1.2 ml of methanesulfonyl chloride in 10 ml of methylene chloride is stirred dropwise at room temperature into a mixture of 3 g of 1-(4-aminophenyl)-3-azabicyclo[3.1.0]hexane-2,4-dione, 90 mg of dimethylaminopyridine and 37 ml of pyridine. After it has been stirred for 16 hours, the reaction mixture is freed from solvent in vacuo. The residue is dissolved in 100 ml of water and the solution is adjusted to pH 1 with hydrochloric acid. After further stirring, the crystals are isolated by filtration and recrystallised from methanol. The title compound is obtained in the form of whitish orange crystals with a melting point of 208°–209° C. and with Rf=0.32 on thin-layer silica gel plates in the system methylene chloride/methanol (10:1).

EXAMPLE 23

1-(4-Acetylaminophenyl)-3-methyl-3-azabicyclo[3.1.0-]hexane-2,4-dione 100 ml of a 0.3N solution of diazomethane in ether are stirred dropwise into a solution, cooled to 0° C., of 2.3 g of 3-(4-acetylaminophenyl)-2,5-dihydro-1H-pyrrole-2,4-dione in 200 ml of tetrahydrofuran, and the mixture is stirred for 16 hours in an ice bath. The crystallised product is filtered with suction, washed with ether, and suspended in 60 ml of ethanol. This mixture is heated for 20 minutes under reflux, filtered and cooled. The white crystals are isolated by filtration, affording the title compound, which is identical with the title compound of Example 19.

EXAMPLE 24

1-(4-N-Acetyl-N-methylaminophenyl)-3-azabicyclo[3.1.0]-hexane-2,4-dione

A mixture of 3.9 g of 1-(4-methylaminophenyl)-3-azabicyclo[3.1.0]hexane-2,4-dione, 180 ml of tetrahydrofuran, 0.2 g of dimethylaminopyridine and 2 ml of acetic anhydride is stirred for 20 hours at room temperature. Then 5 ml of ethanol are added to the reaction mixture, which is stirred for another 30 minutes and subsequently concentrated. The residue is partitioned twice between 500 ml of ethyl acetate and 50 ml of water. The combined organic phases are dried over magnesium sulfate, filtered, concentrated and crystallised from ethyl acetate. The title compound is obtained in the form of white crystals with m.p. 194°–195° C. and with Rf=0.35 on thin-layer silica gel plates in the system methylene chloride/methanol (10:1).

EXAMPLE 25

1-(4-N-Acetyl-N-methylaminophenyl)-3-methyl-3-azabicyclo[3.1.0]hexane-2,4-dione 1.7 g of 1-(4-acetylmethylaminophenyl)-3-azabicyclo[3.1.0]hexane-2,4-dione are dissolved in 40 ml of dimethylformamide and to this solution are added 216 mg of sodium hydride under nitrogen. After it has been stirred for 30 minutes at room temperature, the mixture is cooled to 0° C. and 0.9 ml of methyl iodide are added. The reaction mixture is stirred for 1 hour at 0° C. and then for 20 hours at room temperature. Excess sodium hydride is destroyed with methanol and the mixture is subsequently freed from solvent in vacuo. The residue is partitioned between ethyl acetate/water and a dilute aqueous solution of sodium chloride. The aqueous phases are washed once with ethyl acetate. The combined organic phases are dried over magnesium sulfate, filtered and concentrated. The residual oil is degassed for several hours in a high vacuum at about 40° C., affording the title compound in the form of a yellow, viscous resin with Rf=0.36 on thin-layer silica gel plates in the system methylene chloride/methanol (15:1).

EXAMPLE 26

1-(4-Dimethylaminophenyl)-3-methyl-3-azabicyclo[3.1.0]hexane-2,4-dione and 1-(4-methylaminophenyl)-3-methyl-3-azabicyclo[3.1.0]hexane-2,4-dione 2.16 g of 1-(4-methylaminophenyl)-3-azabicyclo[3.1.0]hexane-2,4-dione are dissolved in 50 ml of dimethylformamide and 300 mg of sodium hydride are added, under nitrogen, to the solution. The mixture is stirred for 30 minutes at room temperature and then a solution of 0.95 ml of methyl iodide in 10 ml of dimethylformamide is added dropwise at 0° C. The reaction mixture is stirred overnight at room temperature. Excess sodium hydride is destroyed with a small amount of methanol and the solvent is stripped off. The residue is partitioned twice between ethyl acetate and an aqueous solution of sodium chloride and the organic phases are dried over magnesium sulfate, filtered and concentrated. The residue is chromatographed on silica gel with a 1:1 mixture of hexane/ethyl acetate, affording fraction I with Rf=0.35 and fraction II with Rf=0.25 on thin-layer silica gel plates in the system ethyl acetate/hexane (1:1). Recrystallisation of fraction I from ether yields 1-(4-dimethylaminophenyl)-3-methyl-3-azabicyclo[3.1.0]hexane-2,4-dione in the form of white crystals with m.p. 140°.141° C. Recrystallisation of fraction II from ethyl acetate/petroleum ether yields 1-(4-methylaminophenyl)-3-methyl-3-azabicyclo[3.1.0]hexane-2,4-dione in the form of white crystals with m.p. 128°–129° C.

EXAMPLE 27

1-(4-Acetylaminophenyl)-3-allyl-3-azabicyclo[3.1.0]hexane-2,4-dione 1.2 g of 1-(4-acetylaminophenyl)-3-azabicyclo[3.1.0]hexane-2,4dione are dissolved in 25 ml of dimethylformamide and to this solution are added 180 mg of sodium hydride under nitrogen. The mixture is stirred for 1 hour at room temperature. The clear, pale yellow solution is cooled in an ice-water bath and then a solution of 0.65 ml of allyl bromide in 5 ml of dimethylformamide is added dropwise. The reaction mixture is stirred overnight and then the solvent is stripped off. The residue is partitioned twice between ethyl acetate and water. The organic phases are dried over magnesium sulfate, filtered and concentrated, and the residue is crystallised from ethyl acetate/ether/petroleum ether. The title compound is obtained in the form of white crystals with a melting melting point of 113°–116° C. and with Rf=0.33 on thin-layer silica gel plates in the system methylene chloride/methanol (10:1).

EXAMPLE 28

1-(4-Aminophenyl)-3-allyl-3-azabicyclo[3.1.0]hexane-2,4-dione

A mixture of 2.2 g of 1-(4-acetylaminophenyl)-3-allyl-3-azabicyclo[3.1.0]hexane-2,4-dione, 8 ml of water and 8 ml of concentrated hydrochloric acid is stirred for 3 hours at 100° C. The mixture is diluted with a small amount of water, cooled in an ice-water bath, made alkaline with 30% sodium hydroxide solution, and extracted twice with ethyl acetate. The organic phases are washed repeatedly with water and once with a concentrated aqueous solution of sodium chloride, dried over magnesium sulfate and filtered. The filtrate is concentrated and the residue is crystallised from ethyl acetate/petroleum ether. The title compound is obtained in the form of pale beige-coloured crystals with m.p. 104°–106° C. and with Rf=0.57 on thin-layer silica gel plates in the system methylene chloride/methanol (10:1).

EXAMPLE 29

1-(4-Aminophenyl)-3-propargyl-3-azabicyclo[3.1.0]hexane-2,4dione

A mixture of 0.54 g of 1-(4-nitrophenyl)-3-propargyl-3-azabicyclo[3.1.0]hexane-2,4-dione and 1.5 g of tin powder in 4 ml of water and 4 ml of water is stirred for 1 hour at 100° C. The reaction mixture is cooled to room temperature and then diluted with 20 ml of water, filtered, and made alkaline with sodium hydroxide solution. The reaction mixture is extracted with ethyl acetate and the organic phase is washed with a dilute aqueous solution of sodium chloride until neutral, dried over magnesium sulfate and concentrated. The residue is recrystallised from ethyl acetate/petroleum ether, affording the title compound with m.p. 106°–109° C. and with Rf=0.12 on thin-layer silica gel plates in the system hexane/ethyl acetate (1:1).

The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 1.9 ml of propargyl bromide in 50 ml of N,N-dimethylformamide. It has a melting point of 163°–165° C. after recrystallisation from ethyl acetate/petroleum ether and has an Rf value of 0.33 on thin-layer silica gel plates in the system hexane/ethyl acetate (1:1).

EXAMPLE 30

1-(4-Aminophenyl)-3-n-decyl-3-azabicyclo[3.1.0]hexane-2,4-dione

Following the procedure of Example 3, a solution of 6.0 g of 3-n-decyl-1-(4-nitrophenyl)-3-azabicyclo[3.1.0]hexane-2,4-dione in 120 ml of ethanol is hydrogenated in the presence of 0.3 g of 5% palladium on carbon and worked up, affording the title compound which melts at 92°–94° C. after recrystallisation from ethyl acetate. The starting material is synthesised in accordance with Example 3, starting from 4.6 g of 1-(4-nitrophenyl)-3-azabicyclo[3.1.0]hexane-2,4-dione, 0.72 g of sodium hydride (pract. Fluka) and 5.3 ml of 1-decyl bromide. The product is a yellow oil with Rf=0.50 on thin-layer silica gel plates in the system hexane/ethyl acetate (1:1).

EXAMPLE 31

(a)

1S-5R-1-(4-Aminophenyl)-3-azabicyclo[3.1.0]hexane-2,4-dione

Following the procedure of Example 1, a solution of 1.3 g of 1S-5R-1-(4-nitrophenyl)-3-azabicyclo[3.1.0]hexane-2,4-dione in 70 ml of ethanol is hydrogenated in the presence of 0.1 g of 5% palladium on carbon and worked up. Recrystallisation from ethanol affords the title compound with a melting point of 203° C. and $[\alpha]_D^{20} = -66° \pm 1°$ (in methanol, c=0.634).

Preparation of the starting material (b)

1S-5R-(4-Nitrophenyl)-3-azabicyclo[3.1.0]hexane-2,4-dione 1S-2R-1-(4-nitrophenyl)-1,2-cyclopropanedicarboxylic acid ($[\alpha]_D^{20} = -66° \pm 1°$; in methanol, c=0.966) is prepared by nitrating 2.75 g of 1S-2R-1-phenyl-1,2-cyclopropanedicarboxylic ($[\alpha]_D^{20} = -193° \pm 1°$; in methanol, c=1.09) with 3.45 ml of concentrated sulfuric acid and 2 ml of nitric acid. This product is reacted in boiling xylene, in the presence of 1.45 g of urea, to the give the title compound with $[\alpha]_D^{20} = -82° \pm 1°$; in methanol, c=0.967).

EXAMPLE 32

(—)1S-5R-1-(4Aminophenyl)-3-azabicyclo[3.1.0]hexane-2,4-dione and
(+)1R-5S-1-(4-aminophenyl)-3-azabicyclo[3.1.0]hexane-2,4-dione A glass column is charged with 380 g of triacetyl cellulose [prepared e.g. by the method described in Chromatographie 6, 277 (1973)] in a 95:5 mixture of ethanol/water. 400 mg of 1-(4-aminophenyl)-3-azabicyclo[3.1.0]hexane-2,4-dione are added to this column. Chromatography is carried out with a 95:5 mixture of ethanol/water under a pressure of 5–6 bar and a flow rate of 350 ml/h. First the (—) enantiomer which is identical with the title compound of Example 31(a) is eluted, followed by the (+) enantiomer.

The products are isolated separately, filtered over silica gel to remove dissolved triacetyl cellulose, and recrystallised from ethanol.

The (—) enantiomer with m.p. 202°–204° and $[\alpha]_D^{20} = -65° \pm 1°$ (methanol, c=0.5) and the (+) enantiomer with m.p. 198°–201° and $[\alpha]_D^{20} = -65° \pm 1°$ (methanol, c=0.4) are obtained.

EXAMPLE 33

Shellac-coated tablets containing 300 mg of 1-(4-aminophenyl)-3-azabicyclo[3.1.0]hexane-2,4-dione can be prepared as follows:

Composition for 10,000 tablets

| | |
|---|---|
| 1-(4-aminophenyl)-3-azabicyclo[3.1.0]hexane-2,4-dione | 3000.0 g |
| corn starch | 680.0 g |
| colloidal silica gel | 200.0 g |
| magnesium stearate | 20.0 g |
| stearic acid | 50.0 g |
| sodium carboxymethyl starch | 250.0 g |
| water | q.s. |

A mixture of the 1-(4-aminophenyl)-3-azabicyclo[3.1.0]hexane-2,4-dione, 50 g of corn starch and the colloidal silica is worked to a moist composition with a starch paste consisting of 250 g of corn starch and 2.2 kg of demineralised water. This composition is forced through a sieve having a mesh width of 3 mm and dried for 30 minutes at 45° C. in a fluidised bed drier. The dry granulate is pressed through a sieve having a mesh width of 1 mm, mixed with a previously sieved mixture (1 mm sieve) of 330 g of corn starch, magnesium stearate, stearic acid and sodium carboxymethyl starch, and compressed to slightly domed tablets.

The tablets are put into a coating pan with a diameter of 45 cm and sprayed uniformly for 30 minutes with a solution of 20 g of shellac and 40 g of hydroxypropylmethyl cellulose (low viscosity) in 110 g of methanol and 1350 g of methylene chloride. The tablets are dried by simultaneously blowing in warm air of 60° C.

Instead of using the compound indicated in this Example, it is also possible to use the same amount of a compound of any of the other preceding Examples.

What is claimed is:

1. A compound of the formula

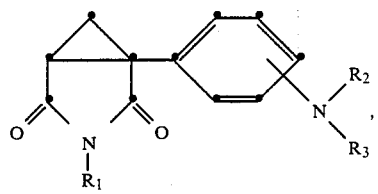
(I)

wherein $R_1$ is $C_1$–$C_{18}$ alkyl, $C_2$–$C_{18}$ alkenyl, $C_2$–$C_7$ alkynyl, $C_3$–$C_{10}$ cycloalkyl, $C_3$–$C_{10}$ cycloalkenyl, $C_3$–$C_{10}$ cycloalkyl-$C_1$–$C_7$ alkyl, $C_3$–$C_{10}$ cycloalkyl-$C_2$–$C_7$ alkenyl, or $C_3$–$C_{10}$ cycloalkenyl-lower alkyl;

$R_2$ is hydrogen, $C_1$–$C_7$ alkyl, sulfo, $R^b$—CO—, $R^a$—O—CO—, $(R^b)_2$NCO—, $R^b$SO$_2$—, or $(R^b)_2$NSO$_2$—; wherein $R^a$ and $R^b$ are each, independently $C_1$–$C_{18}$ alkyl, $C_2$–$C_{18}$ aklkenyl, $C_2$–$C_7$ alkynyl, phenyl, phenyl-$C_1$–$C_7$ alkyl, $C_3$–$C_{10}$ cycloalkyl, $C_3$–$C_{10}$ cycloalkenyl, $C_3$–$C_{10}$ cycloalkyl-$C_1$–$C_7$ alkyl, $C_3$–$C_{10}$ cycloalkyl-$C_2$–$C_7$ alkenyl, or $C_3$–$C_{10}$ cycloalkenyl-$C_1$–$C_7$ alkyl; and $R^b$ may also be H; and $R_3$ is H or $C_1$–$C_7$ alkyl, or a pharmaceutically acceptable salt thereof.

2. A method for treating estrogen dependent mammary carcinoma comprising administering to a warm-blooded animal in need of such administration an aromatase-inhibiting effective amount of a compound of claim 1, or a compound of the formula

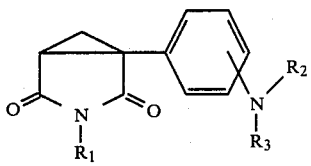

wherein $R_1$ and $R_3$ are hydrogen; and $R_2$ is hydrogen, sulfo, $R^b$CO—, $R^a$—O—CO—, $(R^b)_2$NCO—, $R^b$SO$_2$—, or $(R^b)_2$NSO$_2$—, wherein $R^a$ and $R^b$ are as defined in claim 1 or, a pharmaceuticall acceptable salt thereof.

3. A method of treating estrogen dependent mammary carcinoma comprising administering, to a warm-blooded animal in need of such treatment, an aromatase inhibiting effective amount of a compound of claim 1 or a compound of the formula

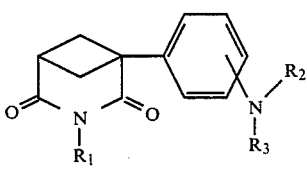
(II)

wherein $R_2$ is hydrogen, sulfo, $R^bCO-$, $R^a-O-CO-$, $(R^b)_2NCO-$, $R_bSO_2-$, or $(R^b)_2NSO_2-$, wherein $R^a$ and $R^b$ are as defined in claim 1 or, a pharmaceuticall acceptable salt thereof.

4. A compound according to claim 1 of formula I, wherein $R_1$ is $C_1-C_{18}$ alkyl, $C_2-C_{18}$ alkenyl, $C_2-C_7$ alkynyl, $C_3-C_{10}$ cycloalkyl, $C_3-C_{10}$ cycloalkenyl, $C_3-C_{10}$ cycloalkyl-$C_1-C_7$ alkyl, $C_3-C_{10}$ cycloalkenyl-$C_2-C_7$ alkenyl, or $C_3-C_{10}$ cycloalkenyl-$C_2-C_7$ alkenyl; $R_2$ is hydrogen, $C_1-C_7$ alkyl, sulfo, $C_1-C_7$ alkanoyl, or $C_1-C_7$ alkanesulfonyl; and $R_3$ is hydrogen or $C_1-C_7$ alkyl; or a pharmceutically acceptable salt thereof.

5. A compound according to claim 1 of formula I, wherein $R_1$ is $C_1-C_{12}$ alkyl, $C_2-C_7$ alkenyl, $C_2-C_7$ alkynyl, $C_3-C_6$ cycloalkyl, or $C_3-C_6$ cycloalkyl-$C_1-C_7$ alkyl; $R_2$ is hydrogen or $C_1-C_7$ alkyl; and $R_3$ is hydrogen or $C_1-C_7$ alkyl; or a pharmaceutically acceptable salt thereof.

6. A compound according to claim 1 of formula I, wherein $R_1$ is $C_1-C_7$ alkyl, $C_2-C_7$ alkenyl, $C_2-C_7$ alkynyl, $C_3-C_6$ cycloalkyl, or $C_3-C_6$ cycloalkyl-$C_1-C_7$ alkyl; and $R_2$ and $R_3$ are hydrogen, or a pharmaceutically acceptable salt thereof.

7. A compound according to claim 1 of the formula I, wherein $R_1$ is methyl, ethyl, n-propyl, isopropyl, n-butyl, isobutyl, n-pentyl, neopentyl, n-heptyl, allyl, 2-propynyl or cyclohexylmethyl; the group $-N(R_2)(R_3)$ is in the 4-position of the phenyl radical and $R_2$ and $R_3$ are hydrogen, or a pharmaceutically acceptable addition salt thereof.

8. 1-(4-Aminophenyl)-3-methyl-3-azabicyclo[3.1.0]hexane-2,4-dione, according to claim 1.

9. 1-(4-Aminophenyl)-3-n-propyl-3-azabicyclo[3.1.0]hexane-2,4-dione, according to claim 1.

10. 1-(4-aminophenyl)-3-isobutyl-3-azabicyclo[3.1.0]hexane-2,4-dione, according to claim 1.

11. 1-(4-Aminophenyl)-3-n-butyl-3-azabicyclo[3.1.0]hexane-2,4-dione, according to claim 1.

12. 1-(4-Aminophenyl)-3-n-pentyl-3-azabicyclo[3.1.0]hexane-2,4-dione, according to claim 1.

13. 1-(4-Aminophenyl)-3-neopentyl-3-azabicyclo[3.1.0]hexane-2,4-dione, according to claim 1.

14. 1-(4-Aminophenyl)-3-n-heptyl-3-azabicyclo[3.1.0]hexane-2,4-dione, according to claim 1.

15. 1-(4-Aminophenyl)3-cyclohexylmethyl-3-azabicyclo[3.1.0]hexane-2,4-dione according to claim 1.

16. A pharmaceutical composition for the treatment of hormonal tumors and gynecomastia comprising an aromatase inhibiting effective amount of a compound of formula I of claim 1, or a pharmaceutically acceptable salt of said compound, together with a pharmaceutically acceptable carrier.

* * * * *